(12) United States Patent
Heimer

(10) Patent No.: US 6,303,086 B1
(45) Date of Patent: Oct. 16, 2001

(54) DISINFECTING WATER BY MEANS OF ULTRAVIOLET LIGHT

(75) Inventor: Richard J. Heimer, Los Angeles, CA (US)

(73) Assignee: Radiant Optics, Inc., Los Angeles, CA (US)

( * ) Notice: Subject to any disclaimer, the term of this patent is extended or adjusted under 35 U.S.C. 154(b) by 0 days.

(21) Appl. No.: 09/429,426

(22) Filed: Oct. 28, 1999

(51) Int. Cl.⁷ ............................................. B01J 19/08
(52) U.S. Cl. ................................................ 422/186.3
(58) Field of Search ....................................... 422/186.3

(56) References Cited

U.S. PATENT DOCUMENTS

| | | |
|---|---|---|
| 4,448,750 | 5/1984 | Fuesting . |
| 4,661,226 | 4/1987 | Mintz et al. . |
| 5,043,080 | 8/1991 | Cater et al. . |
| 5,523,001 | 6/1996 | Foeckler et al. . |
| 5,635,133 | 6/1997 | Glazman . |
| 5,839,078 | 11/1998 | Jennings et al. . |

FOREIGN PATENT DOCUMENTS

WO 99/52566   10/1999  (WO) .

*Primary Examiner*—Kishor Mayekar
(74) *Attorney, Agent, or Firm*—Rockey, Milnamow & Katz, Ltd.

(57) ABSTRACT

In an apparatus for treating unsafe water by exposure to ultraviolet radiation, a reactor vessel has a lower chamber provided with an inlet arranged to admit unsafe water flowing into the lower chamber, an upper chamber disposed above the lower chamber and provided with an outlet to discharge irradiated water from the upper chamber, a treatment surface disposed within the upper chamber and facing upwardly within the upper chamber, and one or more conduits arranged to conduct unsafe water flowing upwardly from the lower chamber over the treatment surface. In the apparatus, a medium-pressure mercury arc discharge lamp is disposed above the treatment surface and is arranged to irradiate unsafe water flowing over the treatment surface. A parabolic reflector disposed above the mercury arc discharge lamp is arranged to reflect ultraviolet radiation downwardly onto unsafe water flowing over the treatment surface. The mercury arch discharge lamp is linear and is disposed along the focus of the parabolic reflector.

6 Claims, 7 Drawing Sheets

DISINFECTING WATER BY MEANS OF ULTRAVIOLET LIGHT

FIELD OF THE INVENTION

The present invention relates to an optical system for disinfecting water and, more specifically, for disinfecting water using ultraviolet light.

BACKGROUND OF THE INVENTION

An adequate supply of drinking water that is free of carcinogens, bacteriophages, and other harmful microorganisms, has been and continues to be a major public health issue.

Although there are several methods known for obtaining potable water, the use of chlorine has been the predominate disinfection agent of choice during the past century. Chlorine is generally used to disinfect tap water, but its propensity for generating carcinogenic by-products such as trihalomethanes has become a serious health problem.

Other treatment methods including the application of ozone or thermal energy are either potentially harmful to the environment or cost ineffective. The application of ultraviolet light, on the other hand, has been demonstrated to be an effective disinfection agent, and in certain cases more effective than chlorine, particularly in the cases of viruses. Ultraviolet radiation has the singular attribute of creating no known toxins.

Whereas the use of chemicals and ozone as a bactericide involves penetration through its cell wall to reach various cellular components, exposure to ultraviolet light does not cause cell death but rather it produces a photo-induced transformation of a cell's nucleic acids causing sterility. Without a reproductive ability, the bacteriophage is not considered to be infectious. The optimum illumination time and light intensity, measured in millijoules/cm$^2$, that is required to sterilize the bacteriophage has been experimentally determined. Any viable ultraviolet disinfection system must exhibit a predetermined exposure (the product of irradiance and time) threshold based on the turbidity factor of water.

The prior art shows many examples of the treatment of water with ultraviolet light. Perhaps the best example in the prior art may be found in about five percent of municipal water treatment plants in the United States. These water treatment plants typically employ an in-ground facility featuring an open channel or sluice (See FIG. 1). Said structure, by virtue of its confines, constricts the flow of water to favorable values of depth and width and rate of flow.

Into this volume of water a plurality of low-pressure mercury discharge lamps 10, each encapsulated within transparent quartz tubing, are immersed in a vertical and perpendicular-to-flow configuration. Said plurality of lamps is arranged into vertical modules placed transversely in the sluice 12 in a uniform array or bank covering both the width and depth of the channel. Typically, there are several lamp banks positioned uniformly in rows along the channel. The required ultraviolet dosage threshold for the water effluent quality determines the number of vertical lamps per channel. This arrangement resembles a sieve through which the water must flow. The angular light distribution of the light emanating from each lamp fills the void between lamps and between rows; irradiating the water as it passes through said voids or interspaces. As the water flows past lamp modules, a sufficient dose is achieved to render the bacteriophage impotent.

Occasionally a horizontal and parallel-to-flow open channel lamp configuration is employed (See FIG. 2). In this configuration, a plurality of lamps 20 is arranged into horizontal modules in a uniform vertical array. The water depth establishes the number of lamps per module. As in the case of the vertical and perpendicular-to-flow configuration, each lamp is encapsulated within transparent quartz tubing. Water flows along the interspaces between lamps 22, experiencing radiation along the length of the low-pressure mercury discharge lamps.

There is yet another example of prior art, shown in FIG. 3, in which a plurality of lamps 30, each encapsulated within transparent quartz tubing, is positioned longitudinally in a horizontal and parallel-to-flow configuration within a cylindrical shaped closed vessel 32. The number of lamps is determined by the inner diameter of the closed vessel. Not unlike the previous example, water flows into the vessel through an inlet pipe 31 receiving radiation as passing along the length of the pipe, exiting as safe water at exit pipe 33. In this prior art example, the device is intended for application where the volume of water to be treated is less than that normally required of a municipal water plant. Said device might satisfy, for example, the needs of a large commercial bottling enterprise.

These prior art examples, despite their demonstrated utility, have several significant drawbacks. First and foremost, the water-contacting surface of the quartz tubing, which isolates the lamp from the water, is prone to an accumulation of particulate matter, salts, minerals and other contaminants (scaling buildup) found in the water. The lamp exitance may be sufficiently absorbed by the inorganic scaling to reduce irradiance below the dose threshold required for sterilization. Second, the scaling buildup on the quartz tubing must be frequently removed requiring heavy maintenance.

In said horizontal and vertical lamp configurations, the cleaning of the lamp modules generally means that the lamp modules must be removed from the channel of chamber (See FIG. 1). A bridge crane 14 is used to carry the lamp modules from the disinfection channel into an acid tank 16 for cleaning. The acid tank must, in turn, be cleaned and the residue discarded in, for example, the disinfection plant's headwaters. Third, ultraviolet light does not transmit efficiently in water even through nominal distances, requiring the separations between lamps to be kept small. As a concomitant result, a large number of lamps are required to affect sufficient dosage for bacteriophage sterilization. Finally, there is a danger of electrical shock owing to the aggregate voltage supplied to the plurality of lamps that must be delivered through immersed electrical conduit.

Thus, a need has arisen for an ultraviolet water disinfection system that avoids the aforementioned drawbacks, particularly, with regard to providing for a longer term, stable level of illuminance consistently sufficient to sterilize bacteriophages.

SUMMARY OF THE INVENTION

This invention provides an apparatus comprising a reactor vessel and a medium-pressure mercury arc discharge lamp, for treating unsafe water by exposure to ultraviolet radiation. This invention eliminates any need to submerge the lamp, as has been the prior art practice.

The reactor vessel has a lower chamber provided with an inlet arranged to admit unsafe water flowing into the lower chamber, an upper chamber disposed above the lower chamber and provided with an outlet to discharge irradiated water from the upper chamber, a treatment surface disposed within the upper chamber and facing upwardly within the upper chamber, and one or more conduits arranged to conduct unsafe water flowing upwardly from the lower chamber over the treatment surface. The lamp is disposed above the treatment surface and is arranged to irradiate unsafe water flowing over the treatment surface.

DETAILED DESCRIPTION OF THE ILLUSTRATED EMBODIMENTS

Figure 1:
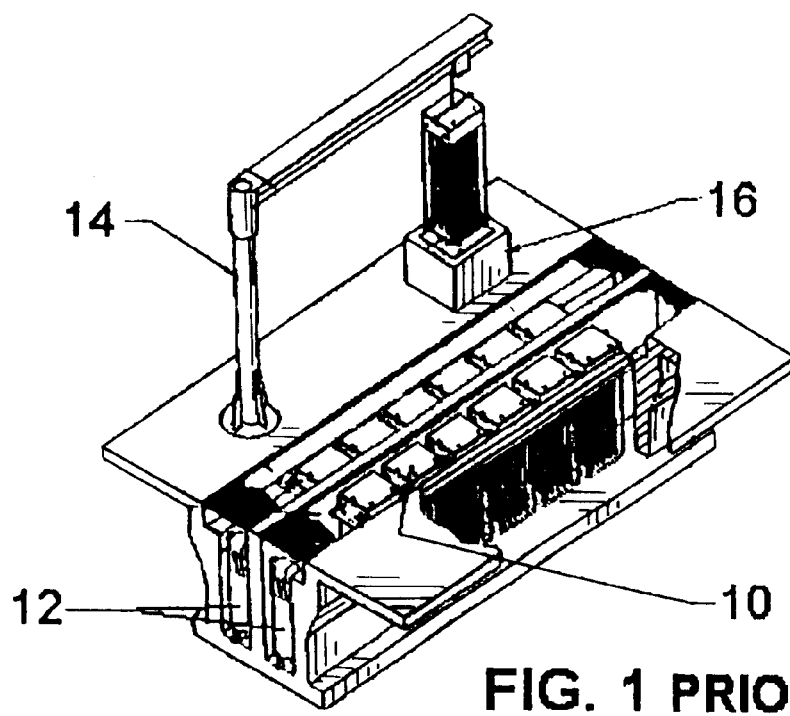
FIG. 1 is a prospective view of a prior art design, in-ground, open channel ultraviolet reactor with lamps arranged in a vertical and perpendicular-to-flow configuration.
Figure 2:
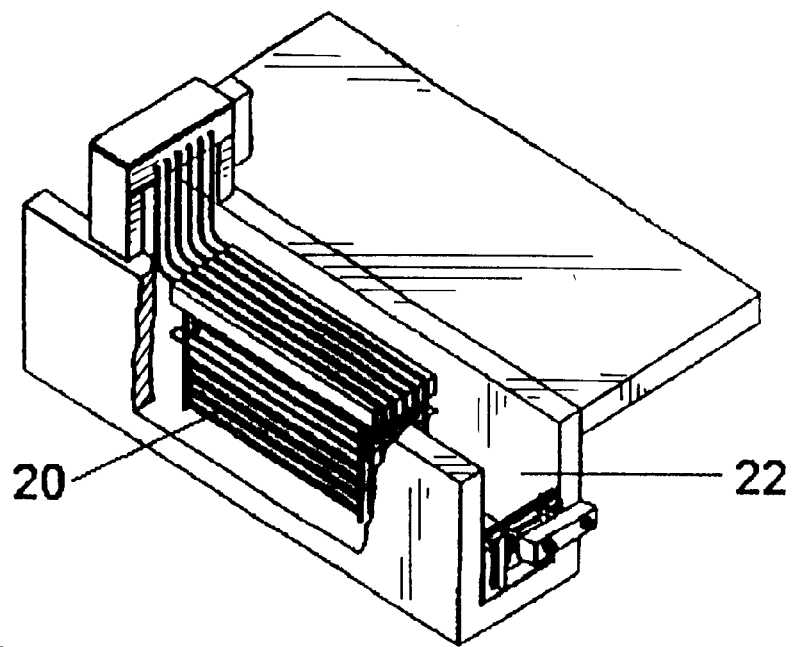
FIG. 2 is a prospective view of a prior art design, in-ground, open channel ultraviolet reactor with lamps arranged in a horizontal and parallel-to-flow configuration.
Figure 3:
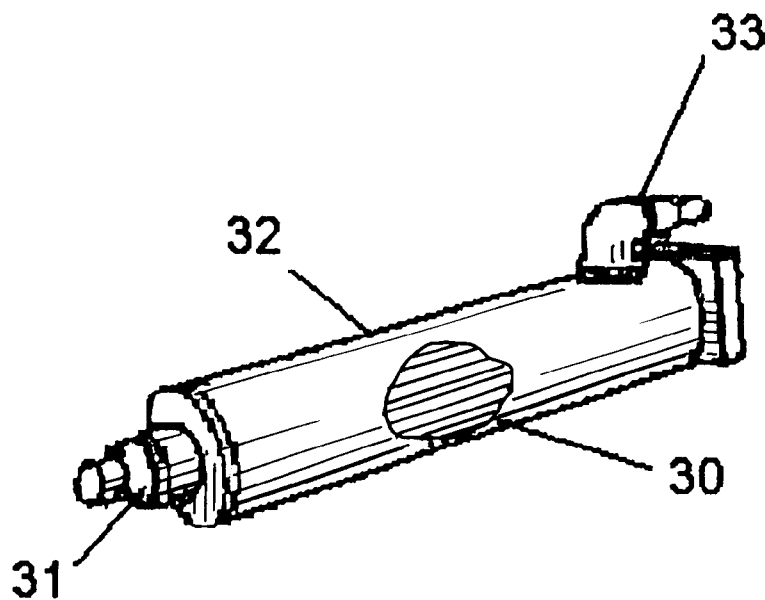
FIG. 3 is a prospective view of a prior art design, closed-vessel, ultraviolet reactor with lamps arranged in horizontal and parallel-to-flow configuration.
Figure 4:
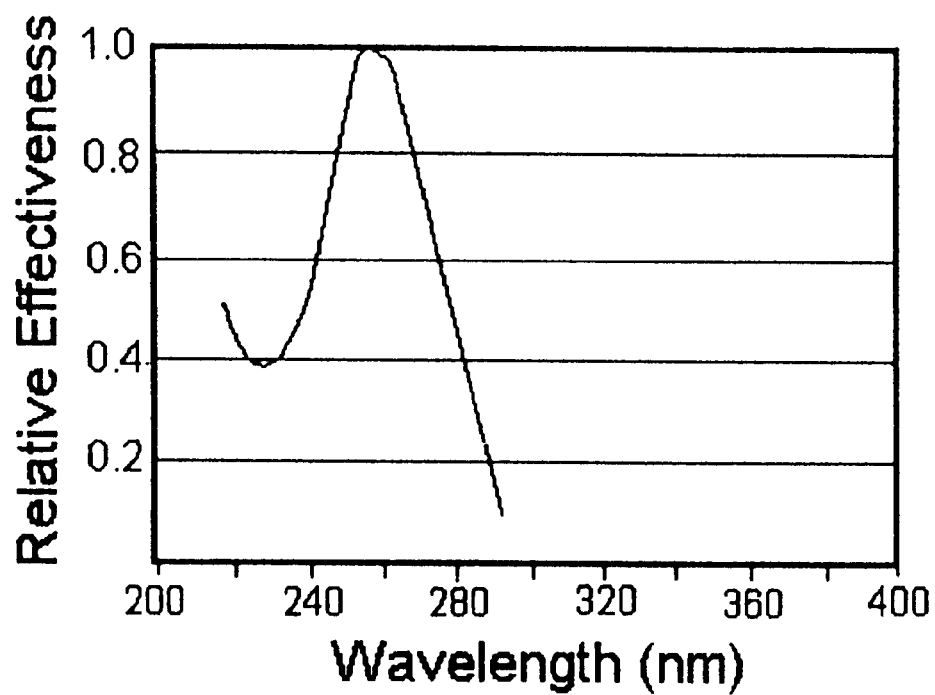
FIG. 4 is graph illustrating the wavelength interval in which bacteriophages are susceptible to photo-induced DNA transformations.

Ultraviolet disinfection is a physical process, as distinguished from a chemical method such as chlorination, that uses electromagnetic energy produced by a light source to prevent the cellular proteins and nucleic acids from further replication. The bactericidal effect of ultraviolet light, as shown in FIG. 4, occurs in the wavelength band from 200 to 300 nanometers.

Figure 5A:
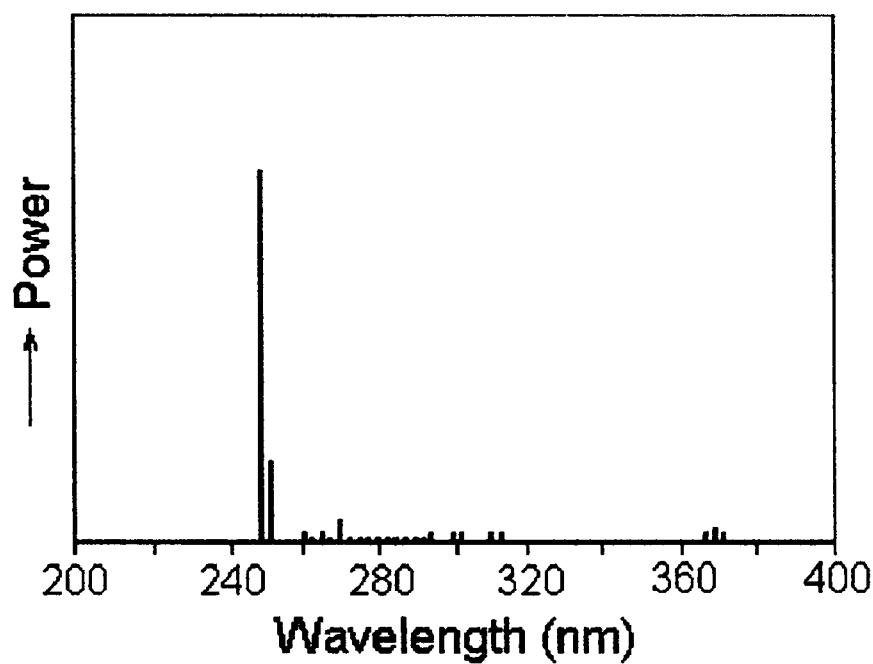
FIGS. 5a and FIG. 5b are plots of the spectral irradiance function of the low-pressure and medium-pressure mercury discharge lamps respectively.
Figure 5B:
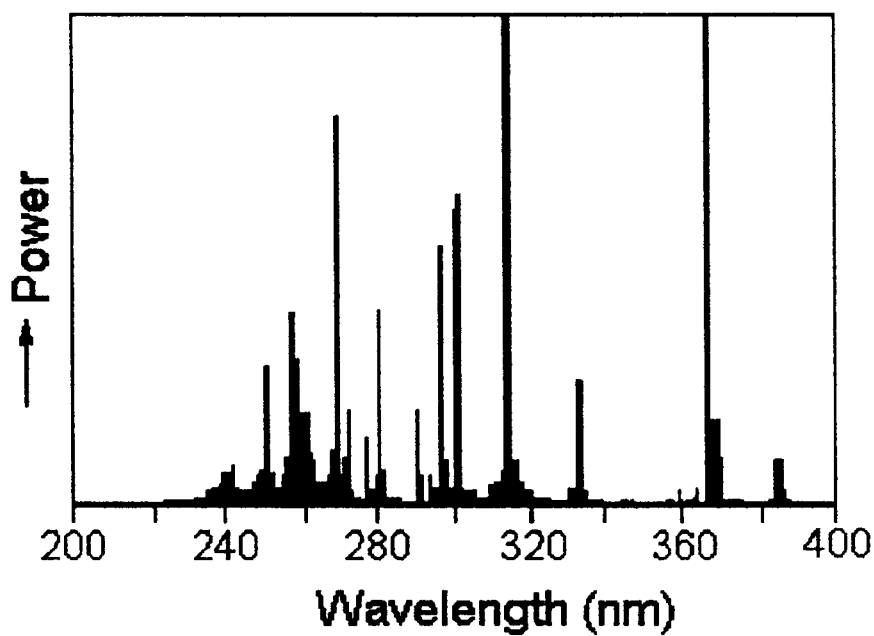

The light source commonly used for ultraviolet disinfection is a mercury arc discharge lamp. The spectral irradiance function of a mercury discharge lamp depends on the pressure at which the arc is operated. In the case of low-pressure lamps, the irradiance is nearly monochromatic, 85 to 90 percent of the total irradiance residing in a narrow band around 273.7 nanometers as shown in FIG. 5a. A medium-pressure mercury arc discharge lamp has a broadened spectrum, as illustrated in FIG. 5b. It will be noticed, however, that there is no irradiance exactly at the wavelength 253.7 nanometers, although there is a continuum of wavelengths throughout most of the bactericidal bandwidth with a strong line occurring at 265 nanometers. A medium-pressure mercury arc discharge lamp produces a much higher intensity over a wider range of germicidal wavelengths. Consequently, a medium-pressure mercury arc discharge lamp may be better suited to disinfecting wastewater of lower quality, such as wastewater with transmissivity values of 50 percent or less. In instances where the water quality is above 50 percent transmittance, one medium-pressure mercury arc discharge lamp may produce a dose equivalent to that produced by several low-pressure mercury arc discharge lamps.

A high-pressure mercury arc discharge lamp is not considered a candidate source for ultraviolet water disinfection because of its inherently wider range of radiation emissions. This means that less of the applied power is being used to produce germicidal wavelengths, resulting in high operating cost.

There are other important physical differences in mercury arc discharge lamps of different pressures. Low-pressure mercury arc discharge lamps, which typically have operating pressures less than two atmospheres, may have electrode separations (arc discharge gaps) of up to one meter. Medium-pressure mercury arc discharge lamps, which typically have operating pressures in a range from about two atmospheres to about three atmospheres, typically have arc gaps of 100 millimeters or more. High-pressure mercury arc discharge lamps, which typically have operating pressures greater than about three atmospheres, typically have arc gaps in a range from 5 to 25 millimeters.

Additionally, the power supply requirements for these lamps are remarkably different. The low-pressure lamp, for example, may be operated with a core and coil ballast. The medium-pressure lamp utilizes a magnetic ballast similar to that used with low-pressure lamps. The high-pressure lamp requires an electronic igniter and ballast to initiate and sustain the arc discharge.

Figure 6:
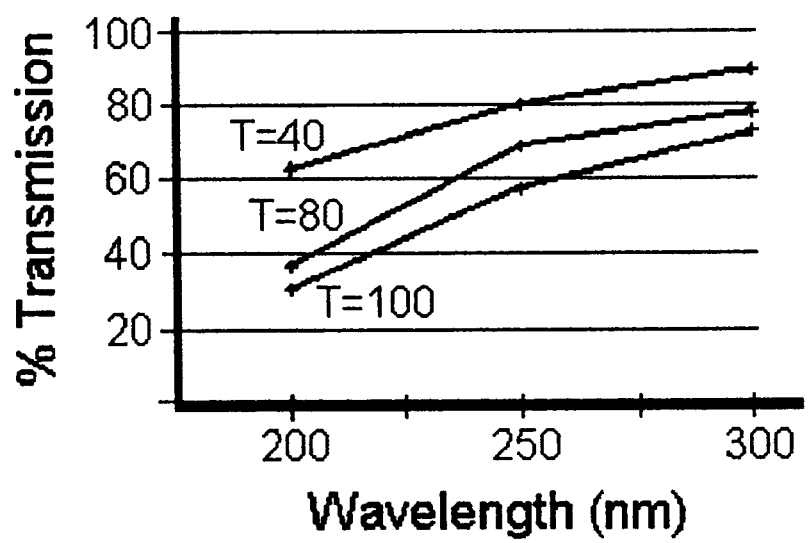
FIG. 6 is a plot of external transmission of distilled water at distances of 40-, 80- and 100-millimeters.

Ultraviolet light is arbitrarily categorized into three bands, according to its anecdotal biological effects. The UV-A bandwidth is from 315 to 400 nanometers. The UV-A is of relatively low energy and is the least harmful radiation. Most phototherapy and tanning booths use UV-A lamps. UV-B bandwidth is from 280 to 315 nanometers. UV-B is the most destructive form of ultraviolet light because it has enough energy to damage biological tissue. It is known to cause skin cancer. The UV-C, with a bandwidth of 100 to 280 nanometers, contains the bacteriocidal band in which water disinfection becomes possible. UV-C light is not efficiently transmitted in air; it is almost completely absorbed within a few hundred meters. The lack of good transmission of UV-C light in water, even in distilled form, is also limited (See FIG. 6). Additionally, the inverse square law limits the light propagation as the depth of the water is increased.

Figure 7:
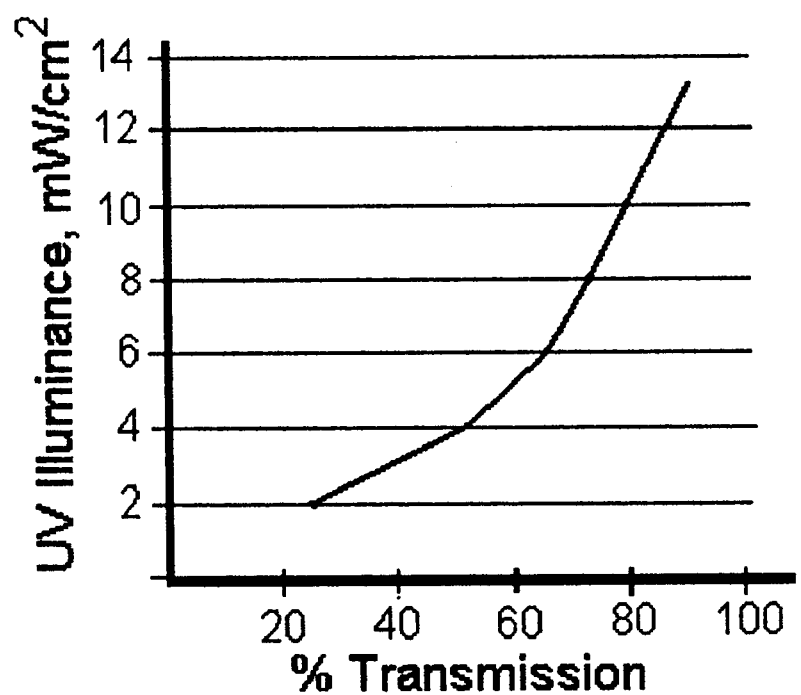
FIG. 7 is a plot of the irradiance at a depth of 75-millimeters of water versus the percent transmission of water (effluency)

The transmission of UV-C light in water, as limited as it is, is affected by water quality parameters such as turbidity and suspended solids, particulate matter size, water hardness and its iron content. FIG. 7 show the average ultraviolet penetration as a function of transmission, in milliwatts per $cm^2$, at a depth of 75 millimeters.

Now to be discussed are the requirements for an effective ultraviolet exposure (the product of irradiance and time) as a function of water effluence. As with chlorination, the ultraviolet dosage is established on results obtained from pilot studies to meet required water quality (effluency). For example, ultraviolet dosages ranging from 30 to 60 mjoules/cm² is required to meet quality criteria for secondary effluents; i.e., from <240 to <23 total coliforms per 100 ml. An ultraviolet dose of at least 120 mjoules/cm² is required to reliably meet a discharge requirement of <2.3 coliforms/100 ml.

A theoretical model for exposure is based on Beer's law, which states:

$$N=N_o e^{-KIT}$$

where N=the total coliforms/100 ml after exposure $N_o$=the total coliforms/100 ml before exposure I=irradiance in mw/cm²

T=exposure time (sec)

K=rate constant

Figure 8:
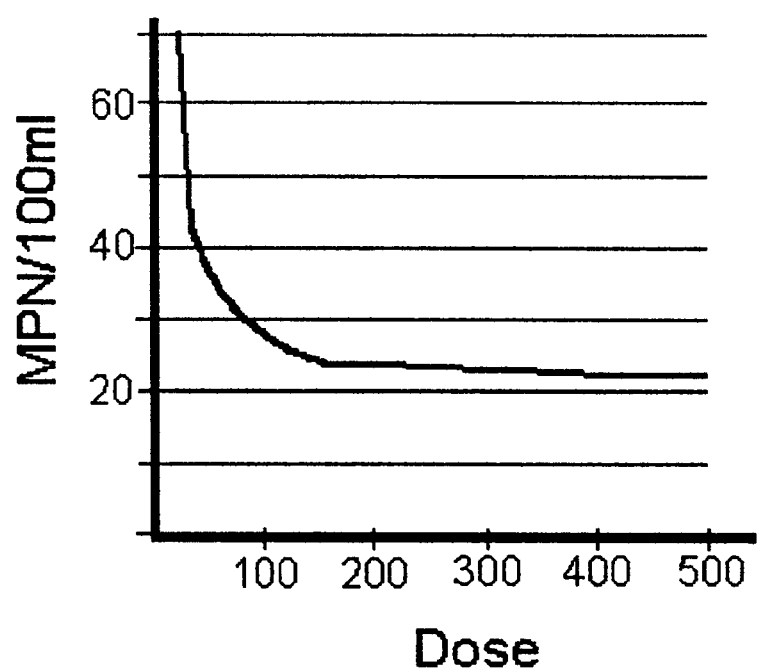
FIG. 8 is a graph illustrating the number of coliforms per unit volume as a function of exposure to ultraviolet light.

In actual practice, however, the results obtained differ from the Beer's prediction. Referring to FIG. 8, a plot of exposure versus the number of coliform per area, it is seen that during the initial exposure stage, the number of coliforms is reduced according to Beer's law. At some point, though, the curve inflects and then maintains a zero slope. The explanation for this behavior is as follows:

The portion of the curve, which corresponds to Beer's law, is thought to represent the ultraviolet exposure that completely penetrates the "free swimming" bacteriophage. The inflection portion of the curve, indicating a decrease in disinfection efficiency is the result of limited ultraviolet exposure to those bacteriophages that are either shadowed or partially buried within suspended particles. The zero slop portion of the curve represents the bacteriophages that are not exposed to ultraviolet radiation because they are totally occulted by or buried within particles in the water.

Thus, the occlusion of bacteriophages within the suspended particles will limit the level of their inactivation by ultraviolet radiation. Generally, increasing the ultraviolet dose will not offset this effect. Filtration of water before treatment will greatly reduce the suspended particle content and improve ultraviolet disinfection efficiency.

Figure 9:
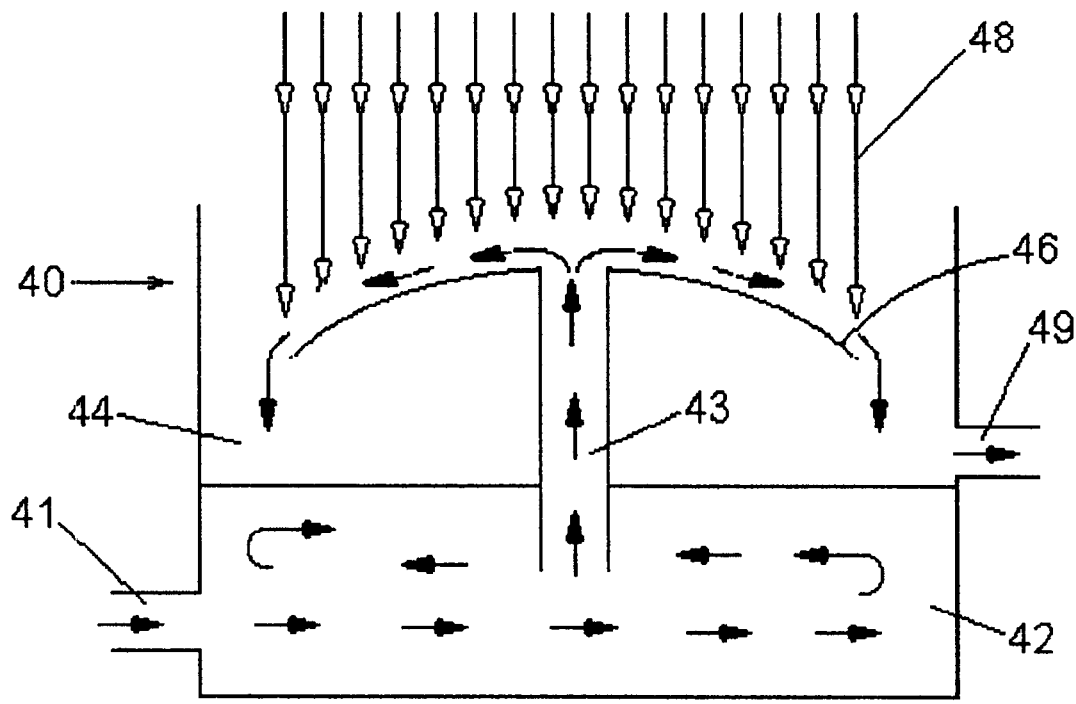
FIG. 9 is an illustration explaining the hydraulic operation of a water-treating apparatus according to the present invention.

As shown in FIG. 9, an apparatus according to the present invention comprises an optical means and a hydraulic means. The optical means comprises of a medium-pressure mercury arc lamp and a reflector, which collects the source of light, organizes it into a beam and projects said beam in a downward vertical direction. The hydraulic means cooperate with the light beam projection by providing a carefully controlled flow rate of water having a uniform depth that is favorable for compete penetration by the light beam.

The hydraulic means 40 comprises a lower inlet chamber 42, an upper outlet chamber 44, and a vertical distribution pipe 43 positioned centrally therebetween, providing a water an access means for one chamber to the other. The axis of the vertical distribution pipe 43 is positioned beneath and parallel to the downwardly projected light beam 48. The distribution pipe 43 protrudes into the upper chamber, its upper end terminating at the intersection of a spherical treatment surface 46, the axis of rotation of which is aligned with the axis of the pipe 43. The spherical treatment surface 46 is wholly contained within the upper chamber and has a cross-section that is several times larger than that of the distribution pipe 43. The cross-section diameter of the treatment surface 46 corresponds to the diameter of the downwardly projected light beam.

The progression of water flow through the present invention is as follows. Unsafe water enters the lower inlet chamber 42 through a pressurized pipe supply 41 and, after having filled the chamber 42, flows into the distribution pipe 43 at its lower end portion, flowing upwardly and subsequently emerging from the distribution pipe 43 at its upper end portion defined by its intersection with the treatment surface 46. The emergent water flows over the treatment surface 46 in a sheeting action, propelled by pressure and gravity, to the treatment surface periphery. whereupon the water falls into the surrounding region of the upper outlet chamber 44. A turbulence generating means, such as a pattern of ridges and grooves, is provided on the treatment surface 46, causing the water flowing over the surface 46 to be agitated and to flow turbulently, thereby increasing the likelihood of exposing partially hidden bacteriophage to ultraviolet light.

The architecture of the present invention provides for a volume of unsafe water of uniformly distributed depth flowing at a steady rate for exposure to ultraviolet light, the depth of said water to be favorably controlled for the complete penetration of the germicidal wavelengths. The inventive treatment surface, in addition to having a surface profile that aids in laminar flow turbulence, may also incorporate a reflective means by which the water is exposed to retrograde ultraviolet radiation from said surface, thereby increasing the feed water's exposure to ultraviolet radiation.

It will also be seen that the downwardly directed ultraviolet radiation, in addition to irradiating the water layer flowing over the entire treatment surface, will also penetrate the water column flowing upwardly through the distribution pipe. This in-column light penetration will further favorably treat the feed water to ultraviolet radiation to the extent (depth) that the water transmission (effluency) will permit.

Unsafe water is treated in the upper portion of the distribution pipe and, more importantly, as it cascades over the treatment surface, thus receiving direct and retrograde germicidal irradiation for disinfection purposes. The irradiated or safe water is collected in the upper chamber 44 for subsequent distribution through an outlet pipe 49 to the end users.

In the preferred embodiment of the present invention, the disinfecting reactor is constructed to cooperate with the more efficient medium-pressure mercury arc lamp. As previously mentioned, the arc gap is relatively large, producing, in effect, a linear source. In order to accommodate the light beam geometry generated by a linear source, the disinfection reactor takes a rectilinear form and assumes a greater constructional complexity.

Figure 10:
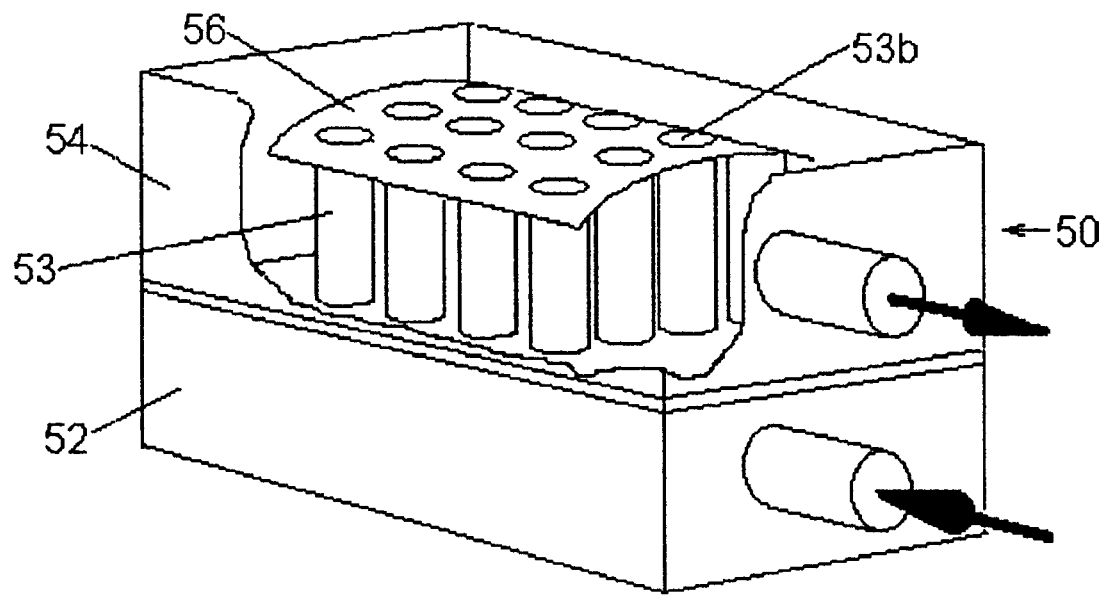
FIG. 10 is a sectional view of the hydraulic means of the water-treating apparatus.

Two chambers 52 and 54, are on top of the other, are utilized as before; however, there are disposed therebetween a plurality of vertical distribution pipes 53 as shown in FIG. 10. The treatment surface 56 is convex, cylindrical in form, and punctuated by a plurality of holes 53b corresponding in number and position to the outlet apertures of the vertical distribution pipes between chambers. This arrangement 50 cooperates with the oval cross-section of the light exposure beam, as produced by a linear source, as well as providing both increased capacity and a favorable flow rate uniquely useful in a large variety of disinfection applications.

Figure 11:
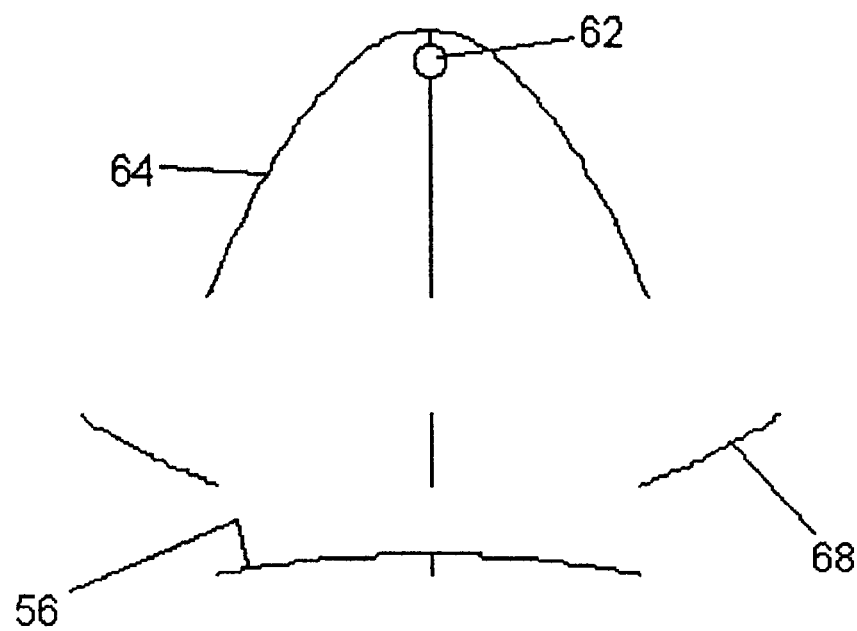
FIG. 11 is a cross-sectional view of the optical means of the water-treating apparatus.

The optical means 60 of the present invention is illustrated as a cross-sectional schematic in FIG. 11. The optical means is composed of a light source 62, located at the focus of a parabolic reflector 64, a treatment surface 56 and positioned therebetween is a retro-reflecting mirror 68, constructed as an annulus. said optical means is situated at a controlled distance above the treatment surface.

For sake of clarity in discussing the optical means of the present invention, the light source will be considered a point. Further, it will be assumed that said light source has an angular light distribution characteristic that radiates uniformly in all directions about said point source, encompassing 4 π steradians. In the plane of FIG. 11, defined as the Y-Z plane, said angular light distribution characteristic surrounds the source, covering an angular extent of 360°.

Figure 12:
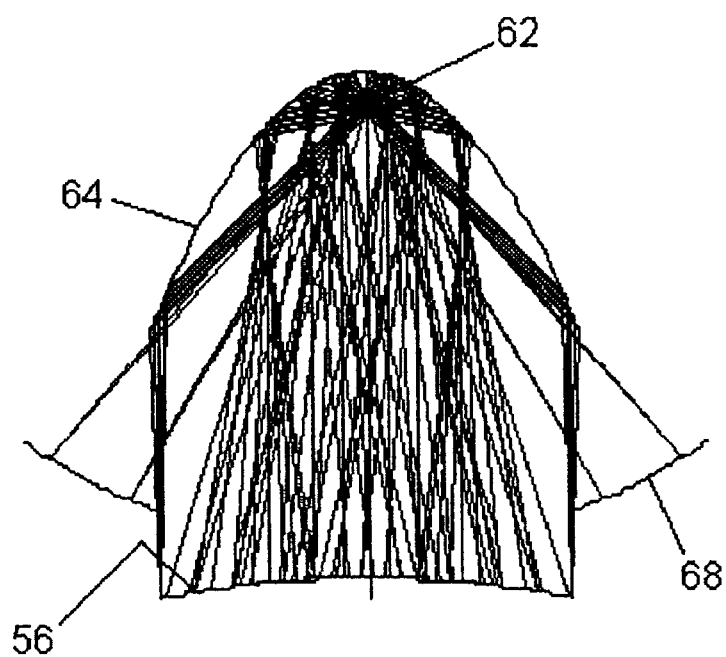
FIG. 12 is a cross-sectional view of the optical means, showing the ray tracings of the direct and reflected light incident on a treatment surface.

Now, with the aid of FIG. 12, the functionally of the various optical surfaces of the optical means 64 will be discussed. It is seen from the ray tracings that the portion of said angular light characteristic that subtends the treatment surface 56 (approximately 45° in azimuth) receives the downward ultraviolet radiation directly. An angular portion amounting to about 270° in azimuth is collected by a parabolic reflector 64, the vertex of which is positioned above the light source 62 a focal distance removed. This surface reflects and directs the ultraviolet radiation in a downwardly direction, indirectly irradiating the treatment surface.

There is still another angular portion of the angular light distribution characteristic that would not be collected and would otherwise be lost were it not for a concave spherical retro-reflector 68 positioned between the parabolic mirror 64 and the treatment surface 56. The reflecting surface 68 is adapted to collect and reflect that annular portion of the light source's exitance (approximately 45°) that neither directly nor indirectly reaches the treatment surface but returns it to the parabolic mirror wherefrom said retro-reflected light is collected again and downwardly distributed over the treatment surface.

The inventive retro-reflector serves two important purposes. First, it improves the system's light grasp and, hence, system efficiency. Second, it distributes its collected ultraviolet radiation towards surface's periphery, providing additional exposure energy to a region receiving less dosage than that received in the more centrally located zone. This assures that the feed stream of unsafe water receives as uniform an ultraviolet dose over the treatment surface as possible.

In the preferred embodiment of the present invention, the source is linear and the various surfaces of the optical means are adapted to conform to the linear source. For example, the parabolic mirror of FIG. 11 and FIG. 12, has a surface in the Y-Z plane of the page. The parabolic surface in three dimensions is, in fact, a toroidal surface. That is, rotating the curve in the Y-Z plane about an axis parallel to the Y-axis and the intersecting the Z-axis forms the surface. The retro-reflector and the treatment surface, depicted in the Y-Z plant as spherical, are in actually, cylindrical surfaces in three dimensions.

Figure 13:
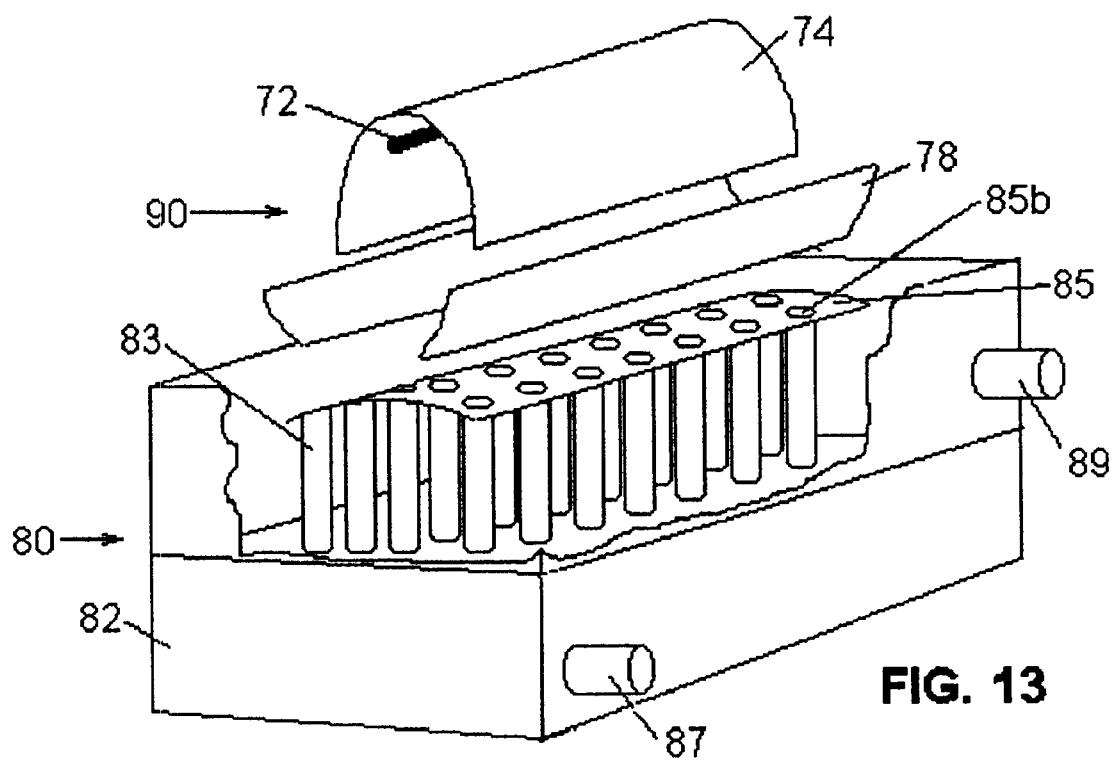
FIG. 13 is a perspective view of a preferred embodiment of the present invention, incorporating both hydraulic and optical means.

Now, the preferred embodiment of the present invention is a water disinfection reactor 100 comprising the optical means 90 and a hydraulic means 80, a prospective view of which is shown in FIG. 13. The hydraulic means comprise an unsafe water feed chamber 82 and a safe water supply chamber 84, said chambers respectively disposed on top of one other. As hereinbefore described a plurality of distribution pipes 83 permit the feed water from the chamber 82 to access and flow over a treatment surface 85 and into the chamber 84. The treatment surface is cylindrical in shape, having a cross-section that cooperates with that of the downwardly directed, incident, ultraviolet beam emanating from the optical means 90.

The treatment surface 85 is provided with a plurality of apertures 85b into which the upper end portions of the distribution pipes 83 access the treatment surface 85. The aperture locations are adapted to favorably control the dwell time, depth, turbulence, and rate of feed water flow over the treatment surface 85. The treatment surface 85 is adapted to enhance the water flow turbulence for favorable exposure of bacteriophage to ultraviolet radiation. Moreover, the treatment surface 85 is adapted to both receive and retro-reflect ultraviolet light into the water feed stream flowing over the treatment surface 85, thereby favorably increasing the germicidal action. Further, the downwardly directed light is also free to enter apertures 53b, penetrating the upwardly flowing water column in the distribution pipes 83 pre-radiating the feed water stream prior to emergence onto the treatment surface.

The optical means 90, which provides the ultraviolet radiation, comprises a medium-pressure mercury light source 72, a toroidal reflector 74, and a cylindrical surface retro-reflector 78. As hereinbefore described, the optical means efficiently collects the source light from a linear lamp and uniformly distributes this light into the unsafe water feed stream. The hydraulic means 80 provides a controlled water feed stream of favorable depth, turbulence, and rate of flow—an assemblage of the optical and hydraulic means making possible the complete ultraviolet light penetration of micro-organisms in said water feed stream.

In summary, it can be seen that the present invention provides a water treatment reactor that remotely delivers ultraviolet radiation for disinfection purposes, thus, eliminating the need for submerging ultraviolet lamps into water as is the prior-art practice.

Various modifications may be made in the embodiments described above without departing from the scope and spirit of the present invention.

What is claimed is:

1. An apparatus for treating unsafe water by exposure to ultraviolet radiation, the apparatus comprising:

(a) a reactor vessel having a lower chamber provided with an inlet arranged to admit unsafe water flowing into the lower chamber, an upper chamber disposed above the lower chamber, a treatment surface disposed within the upper chamber and facing upwardly within the upper chamber, and at least one conduit arranged to conduct unsafe water flowing upwardly from the lower chamber over the treatment surface, the treatment surface being convex and being arranged to reflect ultraviolet light upwardly, (b) a mercury arc discharge lamp disposed above the treatment surface and being arranged to irradiate unsafe water flowing over the treatment surface, and (c) a concave reflector disposed above the lamp and arranged to reflect ultraviolet light downwardly onto unsafe water flowing over the treatment surface.

2. The apparatus of claim 1 wherein the reflector is a parabolic reflector and wherein the mercury arc discharge lamp is linear and is disposed along the focus of the parabolic reflector.

3. The apparatus of claim 1 or 2 wherein the treatment surface is grooved to promote turbulent flow of unsafe water over the treatment surface.

4. The apparatus of claim 3 wherein the treatment surface is cylindrical.

5. The apparatus of claim 1 or 2 wherein the upper chamber is provided with an outlet arranged to discharge irradiated water from the upper chamber.

6. The apparatus of claim 1 wherein the treatment surface is cylindrical.

* * * * *